United States Patent
Kudo et al.

(10) Patent No.: US 6,306,351 B1
(45) Date of Patent: Oct. 23, 2001

(54) NITROGEN OXIDES DETECTION METHOD, AND SENSOR ELEMENT FOR DETECTION OF NITROGEN OXIDES

(75) Inventors: Shuzo Kudo; Katsuki Higaki; Hisao Ohnishi, all of Osaka (JP)

(73) Assignee: Osaka Gas Co., Ltd. (JP)

(*) Notice: Subject to any disclaimer, the term of this patent is extended or adjusted under 35 U.S.C. 154(b) by 0 days.

(21) Appl. No.: 09/214,322

(22) PCT Filed: Jan. 16, 1998

(86) PCT No.: PCT/JP98/00166

§ 371 Date: Jan. 4, 1999

§ 102(e) Date: Jan. 4, 1999

(87) PCT Pub. No.: WO98/32007

PCT Pub. Date: Jul. 23, 1998

(30) Foreign Application Priority Data

Jan. 20, 1997 (JP) .................................... 9-007343

(51) Int. Cl.[7] .................................... G01N 27/00
(52) U.S. Cl. .................... 422/98; 422/83; 422/88; 436/84; 505/181; 505/121; 204/426
(58) Field of Search ............... 422/1–43, 83–98; 505/181; 204/426

(56) References Cited

U.S. PATENT DOCUMENTS

| 5,273,628 | * | 12/1993 | Liu et al. ............... 204/59 |
| 5,554,269 | * | 9/1996 | Joseph et al. ............ 204/424 |
| 5,554,584 | * | 9/1996 | Masumi ................... 505/181 |
| 5,863,503 | * | 1/1999 | Kudo et al. ............... 422/83 |

FOREIGN PATENT DOCUMENTS

| 0632265A | | 4/1995 | (EP) . |
| 2149123A | * | 10/1983 | (GB) . |
| 48054981 | * | 11/1971 | (JP) . |
| 5332971 | | 12/1993 | (JP) . |
| 727730 | | 1/1995 | (JP) . |
| 07140099 | | 2/1995 | (JP) . |
| 8239217 | * | 9/1996 | (JP) . |
| 9288078 | | 11/1997 | (JP) . |
| 9308467 | * | 4/1993 | (WO) . |

OTHER PUBLICATIONS

G. Sberveglieri S. et al., "Bismuth–doped tin oxide thin–film gas sensors", Sensors and Actuators B. vol. 3 (1991) pp. 183–189.

H. Iwahara, T. Esaka et al., Solid State Chemistry 39, (1981) 173–180.

T. Takahashi, H. Iwahara and T. Esaka, J. Electrochemical Society (1977) 1563–1569.

O. Joubert, A. Jouanneaux et al., Solid State Ionics 73, (1994) 309–318.

F. Krok, W. Bougusz et al., Solid State Ionics 70/71, (1994) 211–214.

T. Takahashi, H. Iwahara and Y. Yanagi, J. Applied Electrochemistry 2 (1972) pp. 97–104.

* cited by examiner

Primary Examiner—Jill Warden
Assistant Examiner—Yelena G. Gakh
(74) Attorney, Agent, or Firm—Webb Ziesenheim Logsdon Orkin & Hanson, P.C.

(57) ABSTRACT

The present invention relates to a nitrogen oxide detecting element. Although there has been a demand for effecting detection of a nitrogen oxide by using a semiconductor type gas sensor, no semiconductor type sensors have existed which can detect the nitrogen oxide with good selectivity against other interfering gases (CO, $H_2$) for an extended period of time with good durability. Then, by causing a gas detecting portion to include an oxide containing more than a predetermined amount of Bi and maintaining this gas detecting portion at a temperature range where its electron-conductivity is exhibited, it has become possible to detect the nitrogen oxide.

19 Claims, 10 Drawing Sheets

Fig. 4  embodiment 1 (measurement temperature: 350°C)

Fig. 5

Fig. 7 sensitivity characteristics of embodiment 1 (350°C)

immediately after manufacture of element

Fig. 8 sensitivity characteristics of embodiment 1 (350°C)

after lapse of 1000 hours

NITROGEN OXIDES DETECTION METHOD, AND SENSOR ELEMENT FOR DETECTION OF NITROGEN OXIDES

BACKGROUND OF THE INVENTION

1. Field of the Invention

The present invention relates to the art of detecting nitrogen oxides, more particularly to a method of detecting nitrogen oxides and also a nitrogen oxide detecting sensor element usable in such method.

2. Description of the Related Art

Background Art Relating to Detection of Nitrogen Oxides

Nitrogen oxides are substances which are generated by oxidation of nitrogen present in the air or in a fuel in the course of combustion of the fuel and which are a cause of air pollution. Hence, there has been a strong demand for prevention of their generation and elimination. For restricting emission of nitrogen oxides, needle to say, it becomes necessary to detect/determine their concentrations. For instance, in employing a preventive method by means of adjustment of combustion conditions, the concentrations of nitrogen oxides present in the flue gas need to be monitored in a continuous manner, and the combustion conditions need to be adjusted based on its result. Thus, the art of detecting nitrogen oxide concentrations with high sensitivity is of great importance.

As such nitrogen oxides detecting art noted above, there have heretofore been known electromotive force type sensors utilizing the principle of a concentration cell and semiconductor type sensors using tin oxides ($SnO_2$). However, the known sensors of the electromotive force type, though these provide good sensitivity for nitrogen dioxide ($NO_2$) among the nitrogen oxides, suffer difficulty in detecting NO at lower concentrations. Although the detection of NO too will become possible if NO is converted to $NO_2$, this will result in complexity of the measuring system.

On the other hand, the semiconductor type sensors using tin oxides can determine gas concentration through measurement of its electron conductivity, so that these sensors tend to have a relatively simple construction as a whole. However, as these sensors have the problem of selectivity, as the tin oxides used therein exhibit sensitivities also for other gases than NO, contained in the exhaust gas, such as the sensitivity for carbon monoxide (CO).

Under the state of the art described above, the present inventors have proposed detection of nitrogen oxides by utilizing semiconductor properties of copper complex oxides such as $Bi_2Sr_2CaCu_2O_{8+z}$, which oxides are known as superconducting materials.

Under such circumstances as above, the present inventors studied the possibility of nitrogen oxides detection with various oxides containing Bi. The result, as described hereinafter, showed that for the nitrogen oxides detection, those oxides containing more than a predetermined ratio of Bi specifically sense nitrogen oxides and show resultant change in their electron conductivity if these materials are placed not under a temperature range where they exhibit oxygen-ion conductivity but under a lower temperature range where they exhibit electron-conductivity. The present invention was completed based on this finding. In this respect, it is noteworthy that the material according to this invention has specifically sensitive to nitrogen oxides, while being hardly sensitive to CO, $H_2$ which tend to act as interfering gases in the gas detection.

The present inventors achieved the present invention in the manner described above,. Next, further description will be made on the background art relating to gas detecting capabilities of bismuth oxides.

Background Art Relating to Gas Detecting Art Using Bismuth Oxides $Bi_2O_3$ has long been known to have oxygen-ion conductivity. In order to increase its oxygen-ion conductivity, extensive studies have been made on $Bi_2O_3$ added with foreign atoms (1 T. Takahashi, H. Iwahara and Y. Yanagi, J. Applied Electrochemistry 2 (1972) 97–104, 2 H. Iwahara, T. Esaka and T. Sato, J. Solid State Chemistry 39, 173–180 (1981), 3 T. Takahashi, H. Iwahara and T. Esaka, J. Electrochemical society (1977) 1563–1569) and on complex oxides containing Bi (4 O. Joubert, A Jouanneaux et. al. Solid State Ionics 73 (1994) 309–318, 5 F. Krok, W. Bougusz et. al Solid State Ionics 70/71 (1994) 211–214). $Bi_2O_3$ is formed as a δ phase (cubic) at temperature higher than 730° C., which is the phase transition point, so that it exhibits high oxygen-ion conductivity, but it is formed as an alpha phase (monoclinic) at temperature lower than 730° C., so that its oxygen-ion conductivity is lowered and its p-type conductivity becomes dominant. The biggest subject in the study on this material has been to increase the oxygen-ion conductivity by stabilizing the δ phase by means of additives (Ba, Ca, W, Nb, Ln, etc.).

Accordingly, when this material is used for gas detection, it has been employed solely in the solid electrolyte type gas sensors. Concerning sensors based on the other detection principles, reports have been limited to those concerning a semiconductor type sensor using complex oxides containing other metallic elements than Bi More specific explanation will be given next.

1) those utilizing oxygen-ion conductivity

As an example of application of oxygen-ion conducting material to gas sensors, there are known an oxygen-ion sensor for deriving an electromotive force from a partial pressure difference of oxygen between two electrodes (Japanese patent application Kokai No. Sho. 58-15067) and a sensor having electrodes thereof coated with catalytic layers for allowing selective transmission of a detection-target gas, thus providing sensitivity for the gas. As the oxygen-ion electrolytes employed in these sensors, zirconia is best known. Similar reports have been made regarding bismuth compounds as well In this case, it is necessary to differentiate the oxygen potentials adjacent the surfaces of the two electrodes by providing a partition wall between the opposed electrodes formed on the solid electrolyte so as to separate the detection-target gas and a reference gas from each other or by coating the electrodes with catalysts having differing catalytic activities, so that the element construction tends to be complicated and the costs tend to be high. Further, as the output varies significantly with variation in the oxygen partial pressure, a system will be needed for high-precision control for maintaining the oxygen partial pressure stationary.

With the sensor of this construction, the target gas for detection comprises oxygen or like inflammable gas (CO, $H_2$ or the like). And, as such material exhibits its oxygen-ion conductivity at a temperature higher at least than 400° C., the gas detection is effected at some temperature range higher than said temperature range.

2) those utilizing electron-conductivity

The sensor of this type of construction is referred to as the semiconductor type sensor. In comparison with the solid electrolyte type, this has a simpler element construction which allows its system designing at lower costs. However, there has not been known any art of using $Bi_2O_3$ per se at its electron-conducting range for detecting a gas (especially nitrogen oxides). The reason for this seems to be that $Bi_2O_3$ has conventionally been regarded as near-insulating material rather than as semiconductor material. Namely, since $B_2O_3$ has a very high resistance value at the temperature range (the temperature range relating to the present invention from the room temperature to 400° C.) where it behaves like the p-type semiconductor, studies about its gas sensitivity properties have been nonexistent at all.

On the other hand, corresponding to the above-described material that the present inventors have researched, reports are available concerning use, as a nitrogen oxide sensor, of copper type complex oxides such as $Bi_2Sr_2CaCu_2O_{8+z}$ which contains Bi and Cu as parts of its crystal structure and which is known as a superconducting material (Japanese patent application Kokai No. Hei. 8-21814, Japanese patent application Kokai No. Hei. 8-271467). These materials have the p-type conductivity and provide a higher resistance value (decreased conductivity) when entrapping a nitrogen oxide therein than otherwise. These nitrogen oxide sensor materials having such p-type conductivity comprise complex oxides or compositions which invariably contain copper as an essential component thereof. Hence, the unique interaction thereof has been attributed to the presence of copper therein. For these reasons, as for the material which does not contain Cu in its crystal lattice and contains a relatively high ratio (50 at % or more in terms of metallic element-based conversion) of Bi having no superconducting property, no studies have been made on its sensitivity properties for nitrogen oxides.

SUMMARY OF THE INVENTION

The object of the present invention is to provide a method of detecting a nitrogen oxide which is simple in construction, yet allows selective detection of the nitrogen oxide against interfering gases such as carbon monoxide, hydrogen etc. and which also allows this selective detecting condition to be maintained for an extended period of time and also to provide a nitrogen oxide detecting sensor element usable in this detection.

For accomplishing the above-noted object, a method of the present invention for detecting a nitrogen oxide comprises the steps of:

using a sensor element including a gas detecting portion comprised of a metal oxide containing 50 at. % or more of bismuth as determined by a conversion by the metallic elements basis and electrodes capable of detecting a change in conductivity of the gas detecting portion resulting from contact thereof with the nitrogen oxide; and detecting the nitrogen oxide by detecting change in the conductivity of the gas detecting portion while maintaining the gas detection portion at a temperature range from a room temperature to 400° C.

In the above, "the conversion by the metallic elements basis" means a conversion based on consideration of metallic elements alone (i.e. in the case of an oxide, the amount of oxygen present therein is not considered) and refers to the measure of the amounts of Bi and the other metallic elements in the unit of element. Specifically, supposing the amount of the Bi metallic element is A mol and that of any other metallic element(s) than Bi is B moL the ratio is defined as $A/(A+B) \times 100\%$.

As described hereinbefore, the oxide containing more than a predetermined amount of bismuth specifically (selectively) senses nitrogen oxides and exhibits a change in its resistance, thus being capable of detecting nitrogen oxides. In this respect, the above-described temperature range refers to a temperature range in which the material exhibits the electron-conductivity mainly, not oxygen-ion conductivity. As will be described later in greater details with reference FIG. 6, above this range, the material is hardly sensitive to nitrogen oxides.

On the other hand, a sensor element to be employed in the above-described method comprises a gas detecting portion comprised of a metal oxide containing 50 at. % or more of bismuth as determined by a conversion by the metallic elements basis; electrodes capable of detecting a change in conductivity of the gas detecting portion resulting from contact thereof with the nitrogen oxide; and heating means (sensor-temperature setting means) capable of maintaining the gas detecting portion at a temperature range from a room temperature to 400° C. This element may be suitably used for nitrogen oxides detection.

Preferably, the material (metal oxide) forming the gas detecting portion further contains, as an additive other than bismuth, one or more kinds of elements selected from the group consisting of metallic elements capable of having a valency not greater than 3 and consisting also of In, and Sn.

Further preferably, the material (metal oxide) forming the gas detecting portion further contains, as an additive other than bismuth, one or more kinds of elements selected from the group consisting of Ca, Sr, Ba, Cr, Mn, Fe, Co, Ni, Cu, Zn, Cd, In and Sn.

With addition of such elements cited above, it becomes possible to reduce the resistance value of the sensor element, thus facilitating the detection of change in the resistance value at lower temperature ranges. It becomes also possible to improve the response and recoverability of the sensor element.

In constructing the nitrogen oxide detecting sensor element, the gas detecting portion may be formed as a thin film on the substrate.

Alternatively, the gas detecting portion may be formed by the sintering method.

The above methods both allow increased contacting specific surface area to a flue gas or the like as the detection target gas, thus providing suitable gas detecting portions.

Further, in constructing the gas detecting portion, if this is formed by sintering powder material containing a binder material which does not affect the detection sensitivity, the resultant gas detecting portion will have an increased strength. Specifically, the binder material may be alumina $(Al_2O_3)$, silica $(SiO_2)$, etc.

With the use of binder, such advantages as the increased physical strength and reduced possibility of malfunctioning of the gas detecting portion may be achieved.

For the improvement of the selectivity for nitrogen oxides, it is also preferred that catalyst be provided for restricting any interfering gas other than nitrogen oxides from reaching the gas detecting portion.

With provision of such catalyst, the selectivity of the gas sensor element may be further enhanced. Namely, this catalyst provides the function of oxidizing any component such as CO, $H_2$ etc. which is present in a trace amount in e.g. the flue gas and which component can affect the sensor sensitivity. As the oxidized CO, $H_2$ or the like does not affect the gas sensor sensitivity at all the selectivity and measurement precision may be improved accordingly.

Now, the characterizing feature of the nitrogen oxides detecting method according to the present invention lies in using, for nitrogen oxides detection, such material as conventionally believed to have near-insulating property. Therefore, technique needs to be developed for enabling a relatively high resistance value to be detected with high precision. That is to say, as for the mechanical construction of the element, it is necessary to reduce the distance between the opposed electrodes for enhancing the detecting capability. On the other hand, in the aspect of the material, it is preferred to reduce the resistivity of the gas detecting portion, whose resistance value changes on exposure to nitrogen oxides, in such a manner as not to lose sensing properties for nitrogen oxides.

For the above purposes, the invention provides the following proposals.

Namely, as a proposal concerning the positional relationship between the opposed electrodes used for the resistance detection, regarding the resistance value of the gas detecting portion disposed between the pair of electrodes, it is proposed that the distance between the paired electrodes be set so that the resistance value of the gas detecting portion be $10^6 \Omega$ or less in the atmosphere at its operating temperature (from the room temperature to 400° C.). With this setting, the change in the resistance value developed in the gas detecting portion due to its contact with the nitrogen oxides may be readily determined by means of the existing, well-known detecting method.

As proposals concerning the material, it is proposed that a metallic element capable of having a valency not greater than 3 be solid-dissolved within the crystal lattice of $Bi_2O_3$ so as to increase the p-type conductivity through the effect of valency control thereby to render the inter-electrode resistance $10^6 \Omega$ or less as denoted above in the atmosphere at the operating temperature (from the room temperature to 400° C.). Concerning the resistance value of the gas detecting portion interposed between the paired electrodes, it is also proposed that the gas detecting portion include an electroconductive second phase which does not sense the nitrogen oxides so as to render the resistance value of the gas detecting portion $10^6 \Omega$ or less in the atmosphere at the operating temperature. In this, the second phase comprises e.g. a complex oxide of Bi and Sn, a complex oxide of Bi and In, etc. In this respect, the second phase may be present in the entire gas detecting portion.

In these cases too, the change in the resistance value developed in the gas detecting portion due to its contact with the nitrogen oxides may be readily determined by means of the existing, well-known detecting method.

BRIEF DESCRIPTION OF THE DRAWINGS

FIG. 1 is a schematic view showing construction of a gas detecting element (a) without catalyst, (b)–(c) with a catalyst affixed to the surface of the gas detecting portion and (d) with a catalyst mixed with the powder raw material of the gas detecting element.

DETAILED DESCRIPTION OF THE PREFERRED EMBODIMENTS

Figure 1A:
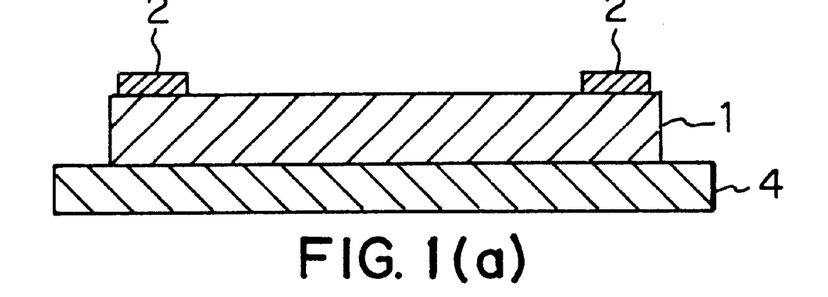
Figure 1B:
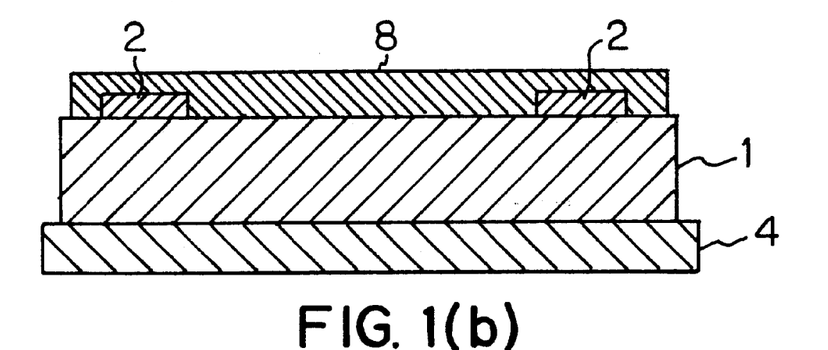
Figure 1C:
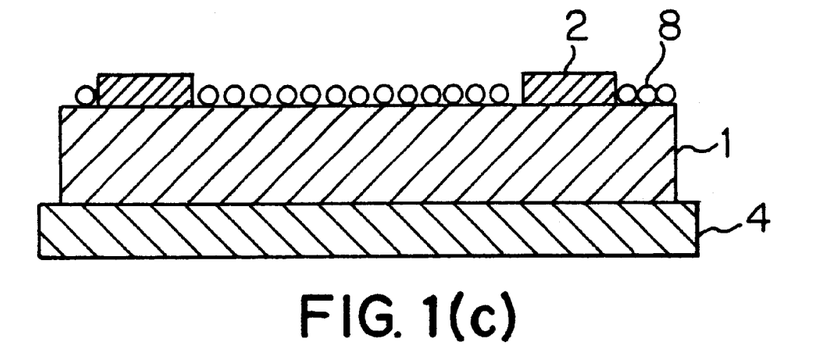
Figure 1D:
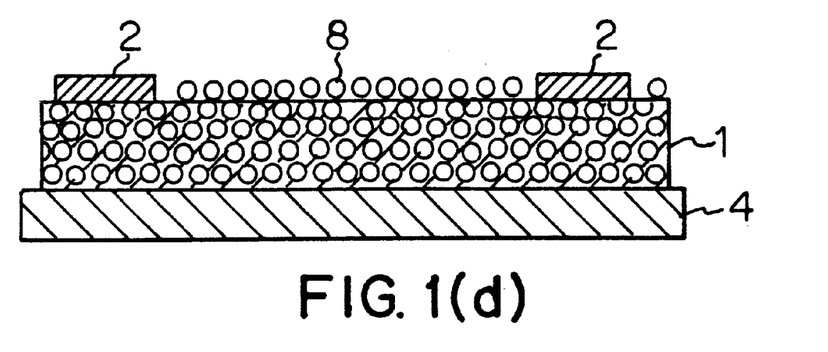
Figure 2:
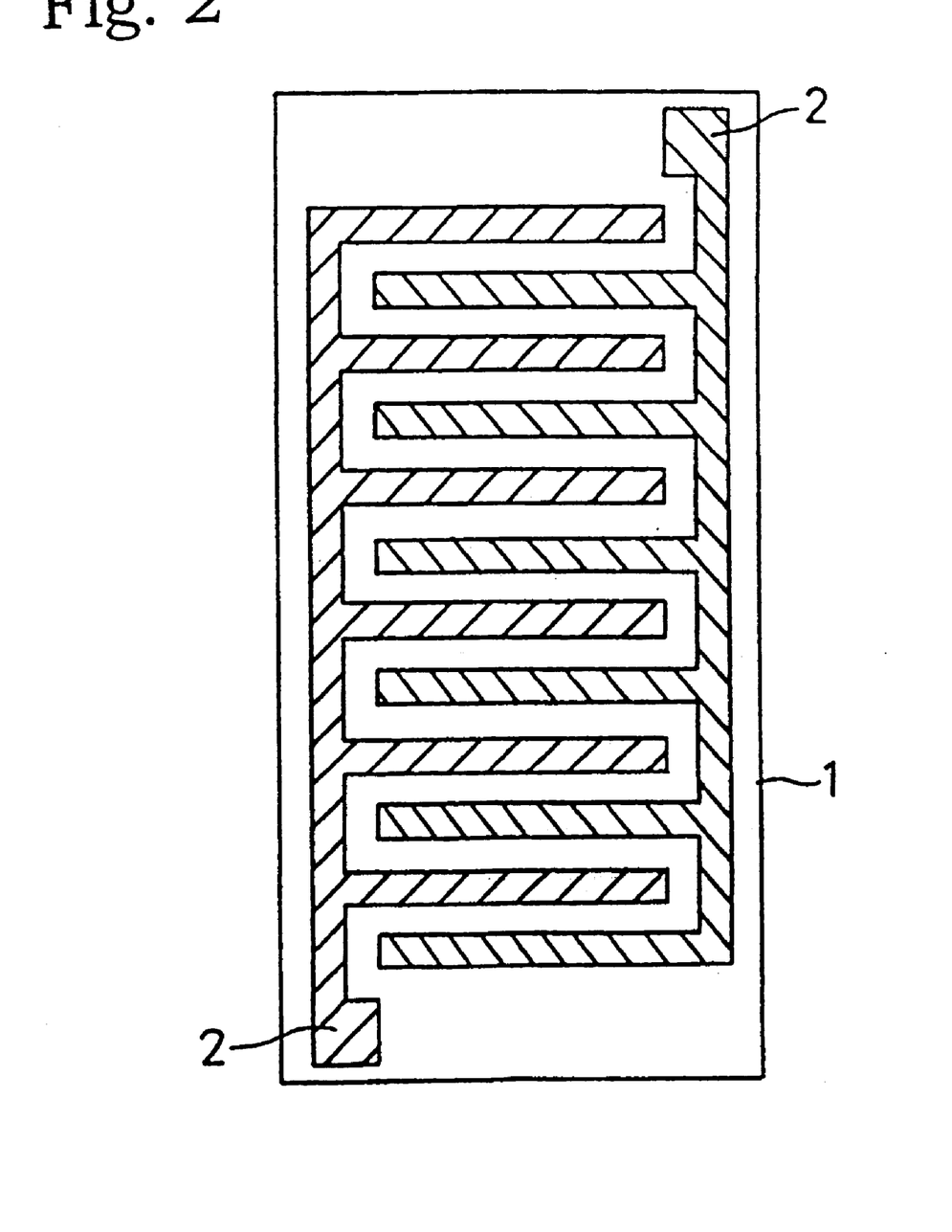
FIG. 2 is a detailed view of an electrode pattern.

An example of a nitrogen oxide detecting sensor element to be used in a nitrogen oxides detecting sensor relating to the present invention will be described with reference to FIGS. 1 and 2. With this sensor, its gas detecting portion 1 is formed by the sintering method, thin-film forming method, or the like.

The gas detecting portion 1 is formed on a substrate 4 which incorporates therein a heater for heating the gas detecting portion 1. The gas detecting portion 1, as shown in FIG. 2, further includes a pair of comb-like electrodes 2. Preferably, the heater may be prepared separately from the substrate and then affixed to one face of the substrate opposite to its face on which the gas detecting portion is attached Alternatively, a layer of the heater and an insulating layer may be formed integrally in the form of a multi-layer construction Further alternatively, the substrate per se may be constructed as a heater member.

As the method of forming the gas detecting portion on the substrate, any known methods such as sintering, thin-film forming method etc. may be employed. The thin-film forming method may specifically be the sputtering, vacuum evaporation, laser ablation, CVD, etc.

Figure 10:
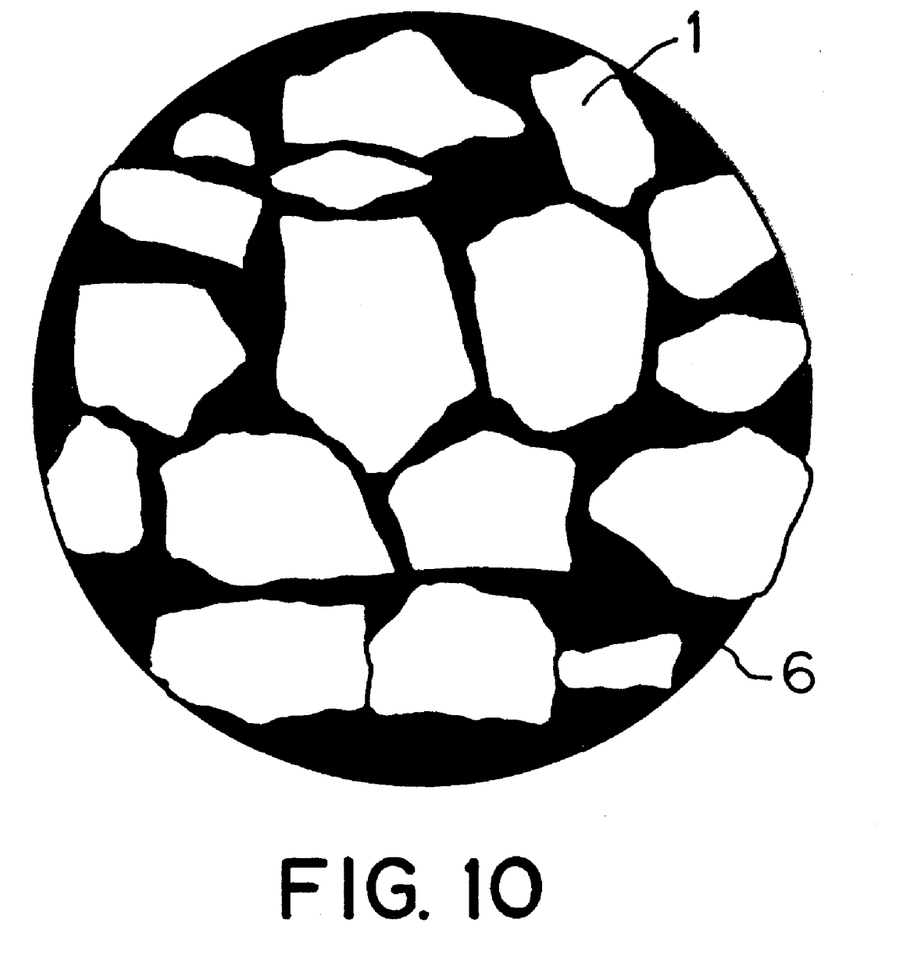
FIG. 10 is a schematic representation of a gas detecting portion incorporating a binder material.

As a binder material and second phase 6 which may be used when the gas detecting portion is manufactured by sintering and which does not affect the sensitivity, alumina ($Al_2O_3$), silica ($SiO_2$), and so on may be cited.

As a material forming a catalyst 8 layer used in the gas detecting portion, a precious metal catalyst of platinum (Pt), palladium (Pd), etc. may be employed. This material may be affixed to the surface of the gas detecting portion. Or, when the gas detecting portion is made by the sintering. Or, when the gas detecting portion is made by the sintering, the material may be mixed with the powder raw material, binder and the like and then sintered to be affixed thereto.

As the material for forming the electrodes of the gas sensor element according to the present invention, a precious metal material often used, such as gold, silver, platinum or the like may be employed, and the electrodes will be attached by the well-known technique to the gas detecting portion formed of the bismuth-containing oxide.

(manufacturing of the gas detecting portion)

In the present embodiment examples (1–18), manufacturing of the gas detecting portion by the sintering method will be described by way of example.

The powder raw materials were weighed and mixed in the compositions recited in the column of composition in Table 1 and then subjected respectively to a preliminary sintering step when necessary. Then, the mixtures were molded under pressure and then subjected to a main sintering step, whereby gas detecting portions were obtained.

TABLE 1 manufacturing conditions of respective embodiment examples

| | composition | group of additive | preliminary sintering temp. | preliminary sintering time period | main sintering temp. | main sintering time period |
|---|---|---|---|---|---|---|
| 1 | $Bi_2O_3$ | | | | 550–630° C. | 3 h |
| 2 | $(Bi_2O_3)_{0.9}(CaO)_{0.1}$ | 2A | 550° C. | 1 h | 700° C. | 3 h |
| 3 | $(Bi_2O_3)_{0.9}(BaO)_{0.1}$ | 2A | 550° C. | 1 h | 650° C. | 3 h |
| 4 | $(Bi_2O_3)_{0.90}(Na_2O)_{0.10}$ | 1A | 550° C. | 3 h | 600° C. | 3 h |
| 5 | $(Bi_2O_3)_{0.90}(K_2O)_{0.10}$ | 1A | 550° C. | 3 h | 600° C. | 3 h |
| 6 | $(Bi_2O_3)_{0.95}(SrO)_{0.05}$ | 2A | 550° C. | 3 h | 650° C. | 3 h |
| 7 | $(Bi_2O_3)_{0.75}(Y_2O_3)_{0.25}$ | 3A | 700° C. | 3 h | 800° C. | 3 h |
| 8 | $(Bi_2O_3)_{0.90}(La_2O_3)_{0.10}$ | 3A(Ln) | 700° C. | 3 h | 800° C. | 3 h |
| 9 | $(Bi_2O_3)_{0.97}(Cr_2O_3)_{0.03}$ | 6B | 550° C. | 3 h | 650° C. | 3 h |
| 10 | $(Bi_2O_3)_{0.95}(MnO_2)_{0.05}$ | 7B | 550° C. | 3 h | 650° C. | 3 h |
| 11 | $(Bi_2O_3)_{0.97}(Fe_2O_3)_{0.03}$ | 8 | 550° C. | 3 h | 650° C. | 3 h |
| 12 | $(Bi_2O_3)_{0.98}(Co_3O_4)_{0.02}$ | 8 | 550° C. | 3 h | 650° C. | 3 h |
| 13 | $(Bi_2O_3)_{0.90}(NiO)_{0.10}$ | 8 | 550° C. | 3 h | 650° C. | 3 h |
| 14 | $(Bi_2O_3)_{0.95}(CuO)_{0.05}$ | 1B | 550° C. | 3 h | 650° C. | 3 h |
| 15 | $(Bi_2O_3)_{0.95}(ZnO)_{0.05}$ | 2B | 550° C. | 3 h | 650° C. | 3 h |
| 16 | $(Bi_2O_3)_{0.95}(CdO)_{0.05}$ | 2B | 550° C. | 3 h | 650° C. | 3 h |
| 17 | $(Bi_2O_3)_{0.90}(In_2O_3)_{0.10}$ | 3A | 550° C. | 3 h | 650° C. | 3 h |
| 18 | $(Bi_2O_3)_{0.90}(SnO_2)_{0.10}$ | 4A | 550° C. | 3 h | 650° C. | 3 h |

(manufacturing of gas sensor element)

On one surface of each gas detecting portion obtained in the manner described above, at least one pair of comb-shaped electrodes 2 were attached. On the other surface of this gas detecting portion 1 opposite to the surface on which the electrodes had been provided, a heating substrate 1 was attached, whereby a sensor was obtained. In this, as for the distance between the pair of electrodes, this distance between the pair of electrodes was set short so that the gas detecting portion interposed between the pair of electrodes may provide the resistance value of $10^6$ Ω or less in the atmosphere at its operating temperature (the room temperature to 400° C.). With this construction, it is possible to detect satisfactorily a change in the relatively high resistance of the bismuth oxide.

(measurement of sensitivity)

As a test gas, a base gas was prepared which had been adjusted to have an oxygen concentration of 11% and a moisture content of 9.5%; then, NO, $H_2$, CO, and $CH_4$ were mixed into this base gas as a gas to be detected.

The gas sensor element was placed in contact with the test gas with heating and maintaining the element at 300–400° C., and a change occurring in the resistance value therein was determined.

(result of measurement)

The results of the measurement of the elements of the respective embodiment examples corresponding to Table 1 are shown in Table 2.

In showing the results in the table, the resistance value ($R_0$) in the base gas is represented in the unit of (Ω); and the sensitivities for NO 500 ppm, $H_2$ 500 ppm, CO 500 ppm are respectively shown. In these, the sensitivity is defined as Rg (resistance value in the test gas)/Ro (resistance in the base gas). Namely, the sensitivity=1 means absence of sensitivity. The farther the sensitivity from 1, the higher the sensitivity.

From the results shown in Table 2, it may be seen that those elements having the gas detecting portions containing more than the predetermined amount of bismuth (75, 90 or 95 at. % or greater) in terms of the metallic elements conversion basis are capable of selectively detecting NO against $H_2$ and CO.

TABLE 2

| | composition | group of additive | operating temp. | resistance value (Ω) | NO 500 ppm | $H_2$ 500 ppm | CO 500 ppm |
|---|---|---|---|---|---|---|---|
| 1 | $Bi_2O_3$ | | 350° C. | 85 k | 4.1 | 1 | 1 |
| 2 | $(Bi_2O_3)_{0.9}(CaO)_{0.1}$ | 2A | 350° C. | 32 k | 2.34 | 1.02 | 1.05 |
| 3 | $(Bi_2O_3)_{0.9}(BaO)_{0.1}$ | 2A | 350° C. | 11 k | 3.49 | 1 | 1.48 |
| 4 | $(Bi_2O_3)_{0.90}(Na_2O)_{0.10}$ | 1A | 350° C. | 10 k | 1.05 | 1 | 1 |
| 5 | $(Bi_2O_3)_{0.90}(K_2O)_{0.10}$ | 1A | 300° C. | 140 k | 1.27 | 1 | 1 |
| 6 | $(Bi_2O_3)_{0.95}(SrO)_{0.05}$ | 2A | 350° C. | 5 k | 2.45 | 1 | 1 |
| 7 | $(Bi_2O_3)_{0.75}(Y_2O_3)_{0.25}$ | 3A | 300° C. | 25 k | 0.91 | 1.04 | 1.01 |
| 8 | $(Bi_2O_3)_{0.90}(La_2O_3)_{0.10}$ | 3A(Ln) | 400° C. | 3.1 k | 1.08 | 1 | 1 |
| 9 | $(Bi_2O_3)_{0.97}(Cr_2O_3)_{0.03}$ | 6B | 350° C. | 60 k | 4 | 1.28 | 1.3 |
| 10 | $(Bi_2O_3)_{0.95}(MnO_2)_{0.05}$ | 7B | 350° C. | 0.93 k | 1.2 | 1.08 | 1.02 |
| 11 | $(Bi_2O_3)_{0.97}(Fe_2O_3)_{0.03}$ | 8 | 350° C. | 76 k | 3.3 | 1.2 | 1 |
| 12 | $(Bi_2O_3)_{0.98}(Co_3O_4)_{0.02}$ | 8 | 350° C. | 3.4 k | 2.45 | 1.22 | 1.1 |
| 13 | $(Bi_2O_3)_{0.90}(NiO)_{0.10}$ | 8 | 300° C. | 11 k | 6 | 1 | 1 |
| 14 | $(Bi_2O_3)_{0.95}(CuO)_{0.05}$ | 1B | 350° C. | 3.7 k | 5.8 | 1.6 | 1.1 |
| 15 | $(Bi_2O_3)_{0.95}(ZnO)_{0.05}$ | 2B | 350° C. | 356 k | 2.3 | 1.2 | 1.4 |
| 16 | $(Bi_2O_3)_{0.95}(CdO)_{0.05}$ | 2B | 350° C. | 2.2 k | 1.68 | 1.1 | 1.1 |
| 17 | $(Bi_2O_3)_{0.90}(In_2O_3)_{0.10}$ | 3A | 350° C. | 20 k | 8.4 | 2.86 | 1.25 |
| 18 | $(Bi_2O_3)_{0.90}(SnO_2)_{0.10}$ | 4A | 350° C. | 30 k | 2.7 | 1.4 | 1.13 |

From the results in Table 2, it may be seen that the selectivity was maintained also with those which provide lower sensitivities than $Bi_2O_3$ without any additives, if they exhibit the p-type conductivity.

Next, there will be described a method of readily determining whether the conductivity is the p-type conductivity or not.

1. With increase in the oxygen partial pressure, the resistance value will decrease.
2. A slight change in the resistance value which occurs in response to a combustible gas indicates the direction of increase of the resistance value.

On the other hand, in the case of the n-type conductivity, the changes in the above respects 1 and 2 are completely opposite. Further, in the case of the oxygen-ion conductivity, without any significant change in the stoichiometric ratio thereof there is generally no change in the respect 1, and it has no sensitivity in the respect 2. At the same time, it develops no sensitivity for NO either.

Incidentally, the particular attention given in the present application to those materials exhibiting the p-type conductivity is based mainly on the background as follows.

Namely, $Bi_2O_3$ without any additives may provide selective sensitivity at 400° C. or lower based on its adsorption phenomenon specific for NO. However, if this is to be formed small and thin, its high resistivity (not the change in the resistance value developed in response to the nitrogen oxide, but its entire resistance) becomes a problem, with the resistance value of the element tending to be high Accordingly, consideration has to be made for reducing the resistivity of the element. As a method for verifying this effect, the effects of various additives were studied intensively.

The methods of reducing the resistivity of $Bi_2O_3$ element may be divided generally into two types, one due to the effect of solid-solution to the $Bi_2O_3$ grains, the other by addition of an electroconductive second phase not affecting the sensitivity. In the case of the former, this may be further classified according to the conductivity mechanism as improvement of one or more of the oxygen-ion conductivity, the p-type conductivity and n-type conductivity. Among these, a particularly preferred embodiment is to significantly increase the p-type conductivity. On the other hand, in the case of the latter type of adding a conductive second phase not affecting the sensitivity, it has been found that the material in which the p-type conductivity is eventually dominant is capable of maintaining effective NO sensing property.

That is, with $Bi_2O_3$ added with a metallic element capable of having a valency not greater than 3, due to its valency controlling effect when solid-dissolved in the crystal lattice of $Bi_2O_3$, the p-type conductivity will be improved (the resistance value will be reduced), whereby detection at a lower temperature range becomes easy (the embodiment examples 2, 3, 4, 5, 6, 9, 10, 11, 12, 13, 14, 15, and 16 correspond to such additive elements). Among these, as for the embodiment examples 5 and 15, the reduction of the resistance value (the valency control effect) is not conspicuous. This is because the added metallic element is deposited therein as a result of not being sufficiently solid-dissolved in $Bi_2O_3$. As for the metallic elements capable of having a valency of 3 or more such as the embodiment examples 17, 18, as these form deposits (the conductive second phases) that do not affect the grain boundary of the crystal grains, the resistance values may be reduced and the selectivity may be maintained.

As the elements capable of having a valency of 3 or more, V and Mo may also be cited. However, the materials added with these elements all exhibit conspicuous n-type conductivity.

As the elements that can be added to the base material of $Bi_2O_3$ for significantly increasing the NO sensitivity, Ni, Cu and so on can be cited.

Next, the particularly preferred embodiment examples will be respectively described in the respect of their sensing properties for nitrogen oxides.

EMBODIMENT EXAMPLE 1 ($Bi_2O_3$)

As a test gas, there was prepared a base gas in which the oxygen concentration and the moisture content had been adjusted to 11% and 9.5% respectively. To this base gas, a gas having NO, $H_2$, CO, $CH_4$ mixed therein at the maximum concentration of 3000 ppm was added. In the measurements, $NO_2$ was at the maximum concentration of 300 ppm, and $CO_2$ was at the concentrations of 5% and 7%.

Figure 3:
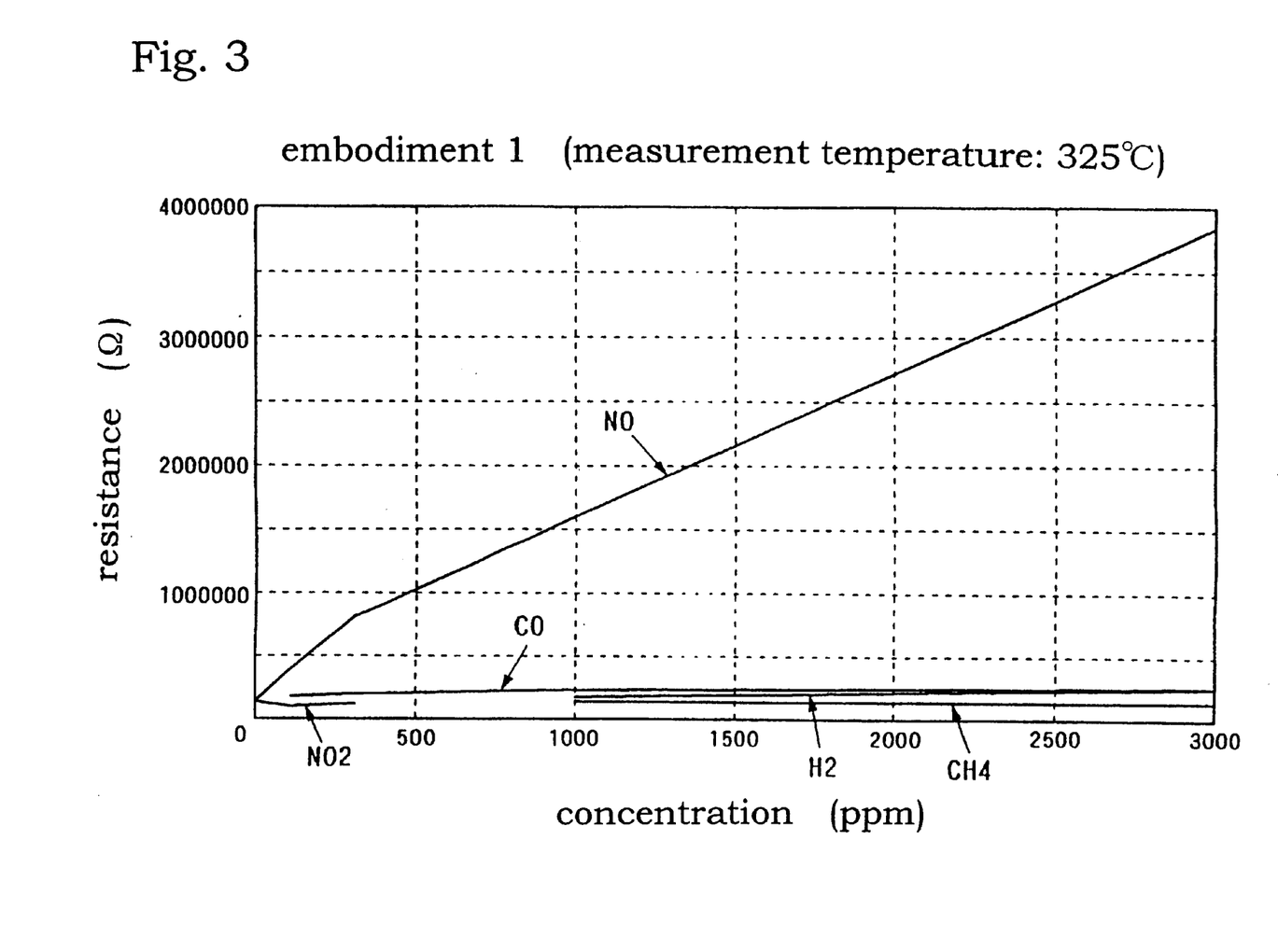
FIG. 3 is a graph showing results of measurements of resistance values conducted by the sensor according to an embodiment 1 on various kinds of gas (measurement temperature 325° C.)
Figure 4:
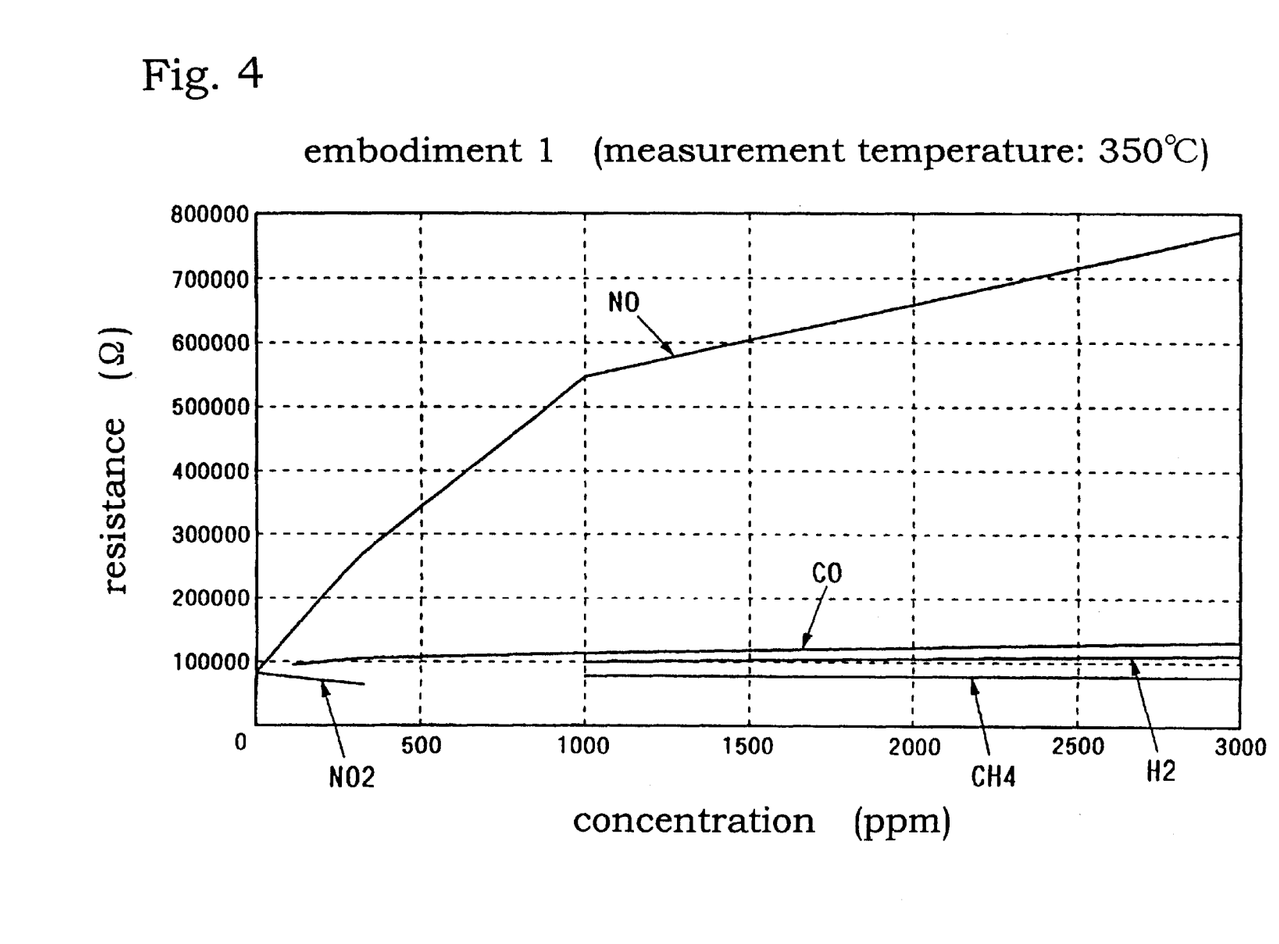
FIG. 4 is a graph showing results of measurements of resistance values conducted by the sensor according to the embodiment 1 on various kinds of gas (measurement temperature 350° C.)

The gas sensor element was heated to and maintained at 325 to 350° C. and was placed in contact with the test gas. The horizontal axis represents the concentration of the detection-target gas in the unit of 1000 ppm, whereas the vertical axis represents the resistance value in the unit of $\Omega$, respectively. FIGS. 3 and 4 show the results of the measurements. It may be seen that the sensor according to the present invention is capable of selectively detecting NO. Although $CO_2$ is not plotted in the graph due to the difference of its concentration range, it was found that the element provided a substantially same resistance value as it was placed in contact with the base gas and also found that its co-existence does not affect the detection of nitrogen oxide.

(evaluation of recoverability)

Figure 5:
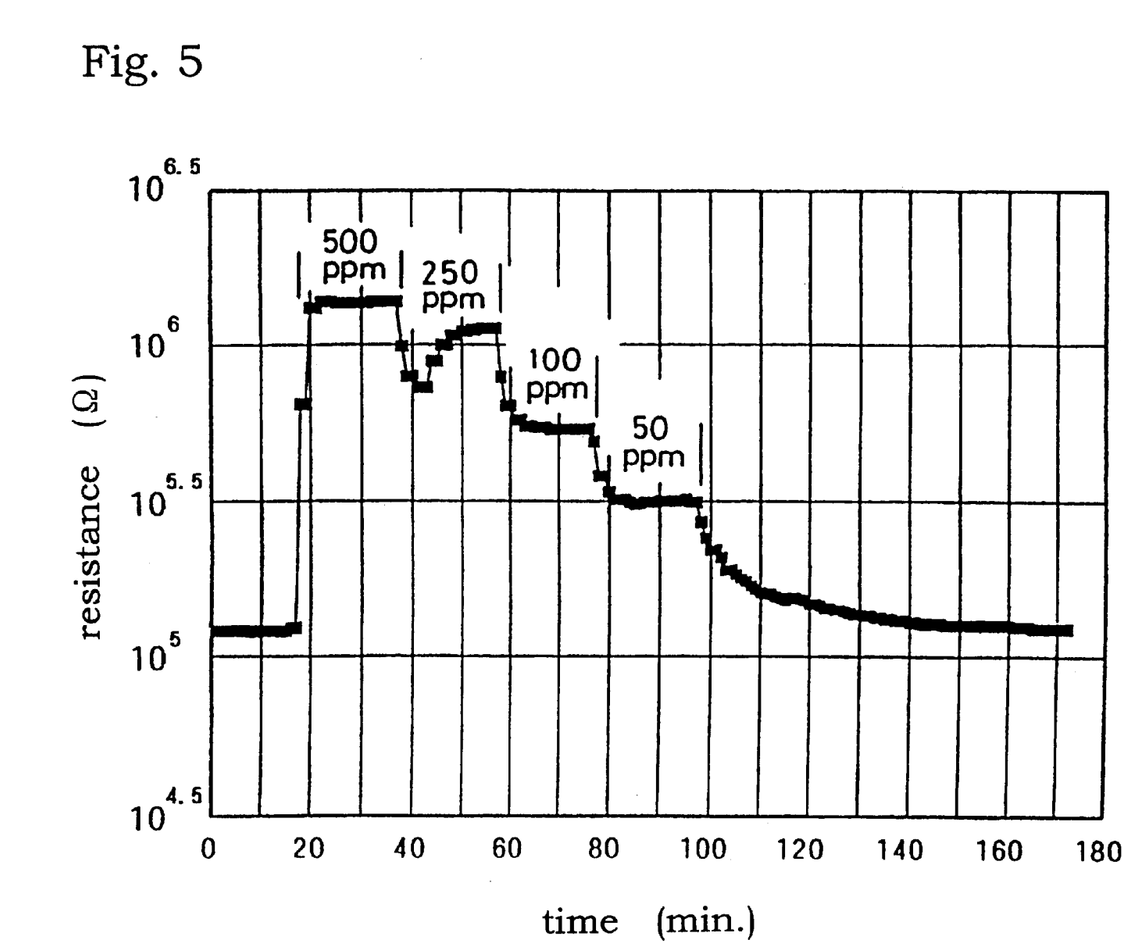
FIG. 5 is a graph showing results of determination of NO response of the sensor according to the embodiment 1.

A sensor needs to recover to the original resistance value when the concentration of the component to be detected becomes zero. Concerning the sensor of embodiment 1, its responses when the sensor was placed in contact with gases having NO concentrations of 500 ppm, 250 ppm, 100 ppm, and 50 ppm were measured respectively. The results of the measurements are shown in FIG. 5. (a trough due to the contacted base gas may be recognized between the contacts with the gases of the two kinds of concentration of 500 ppm and 1000 ppm.) As the sensor eventually recovered its original resistance value when it was contacted with the base gas, it may be understood that the sensor has the recoverability required as a sensor.

(range of operating temperature)

Figure 6:
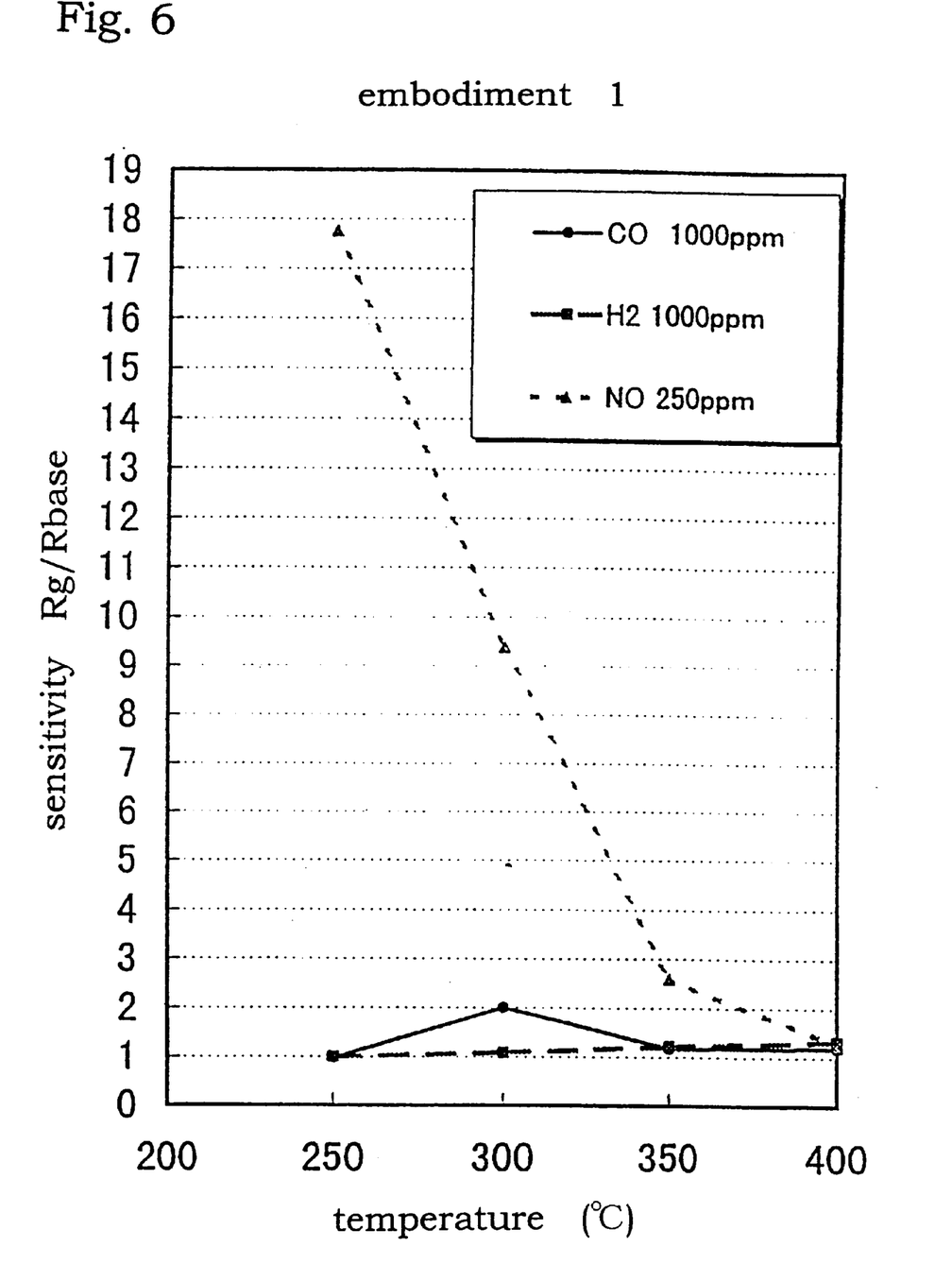
FIG. 6 is a graph showing results of measurements of sensitivities of the sensor according to the embodiment 1 on various kinds of gases at different measurement temperatures.

The relationship between the operating temperature and the sensitivity [Rg (resistance value for the detection-target gas)/ Rbase (resistance value for the base gas)] in this embodiment example is shown in FIG. 6. In this figure, the horizontal axis represents the temperature ° C.) and the vertical axis represents the sensitivity described above.

Further, as for the concentrations of the test gas, the concentrations of NO, $H_2$ and CO were 250 ppm, 1000 ppm, and 1000 ppm, respectively. Therefore, referring to this figure, even when the sensor shows a same sensitivity for the different lands of gases to be detected, the sensor is capable of selectively detecting NO, provided the concentrations are same. As a result, it may be understood that for the selective detection of NO, the temperature range of 250 to 400° C. is preferred In the above temperature range, the electron (hole) conductivity predominates.

On the other hand, when $Bi_2O_3$ was used conventionally as a material for a gas sensor, its operating principle is the sensing principle which can be classified as the solid-electrolyte type, whose essential requirement is being heated at least up to a temperature of 400° C. or higher. On the other hand, the present invention is based on the discovery of the unique phenomenon that the NO sensitivity far exceeds the CO sensitivity at a temperature of the p-type conductivity lower than 400° C. As shown in FIG. 6, at the temperature range lower than 400° C., the NO sensitivity at 250 ppm far exceeds the CO sensitivity at 1000 ppm. And, when the temperature becomes 400° C, the NO sensitivity is reduced and at the same time the sensitivity for the reducing type gas is increased. It is believed that the selective adsorption phenomenon for NO occurs at the temperature range lower than 400° C. In the temperature range from 200° C. to 250° C., the same tendency as described above was maintained In the temperature range not higher than 200° C., although the sensitivity increases, the response, particularly, the recoverability, tends to deteriorate. However, as the response and recoverability are still within the permissible ranges, this temperature range too is usable.

In practice, it is preferred that the sensor element be heated at 200° C. to 350° C.

(durability)

Figure 7:
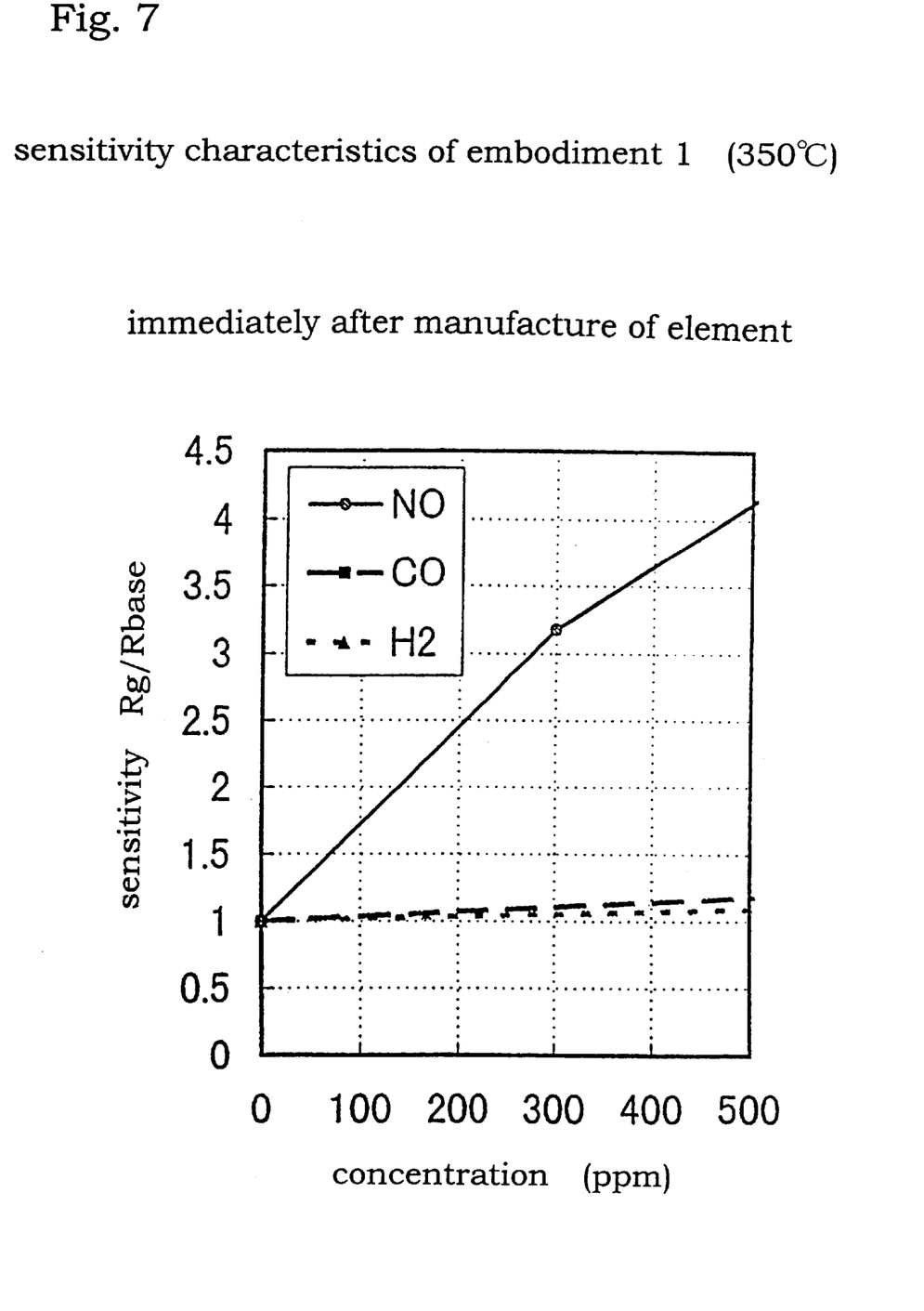
FIG. 7 is a graph showing results of measurements of sensitivities of the sensor according to the embodiment 1 on various kinds of gases at various concentrations (immediately after the manufacture of the sensor element)
Figure 8:
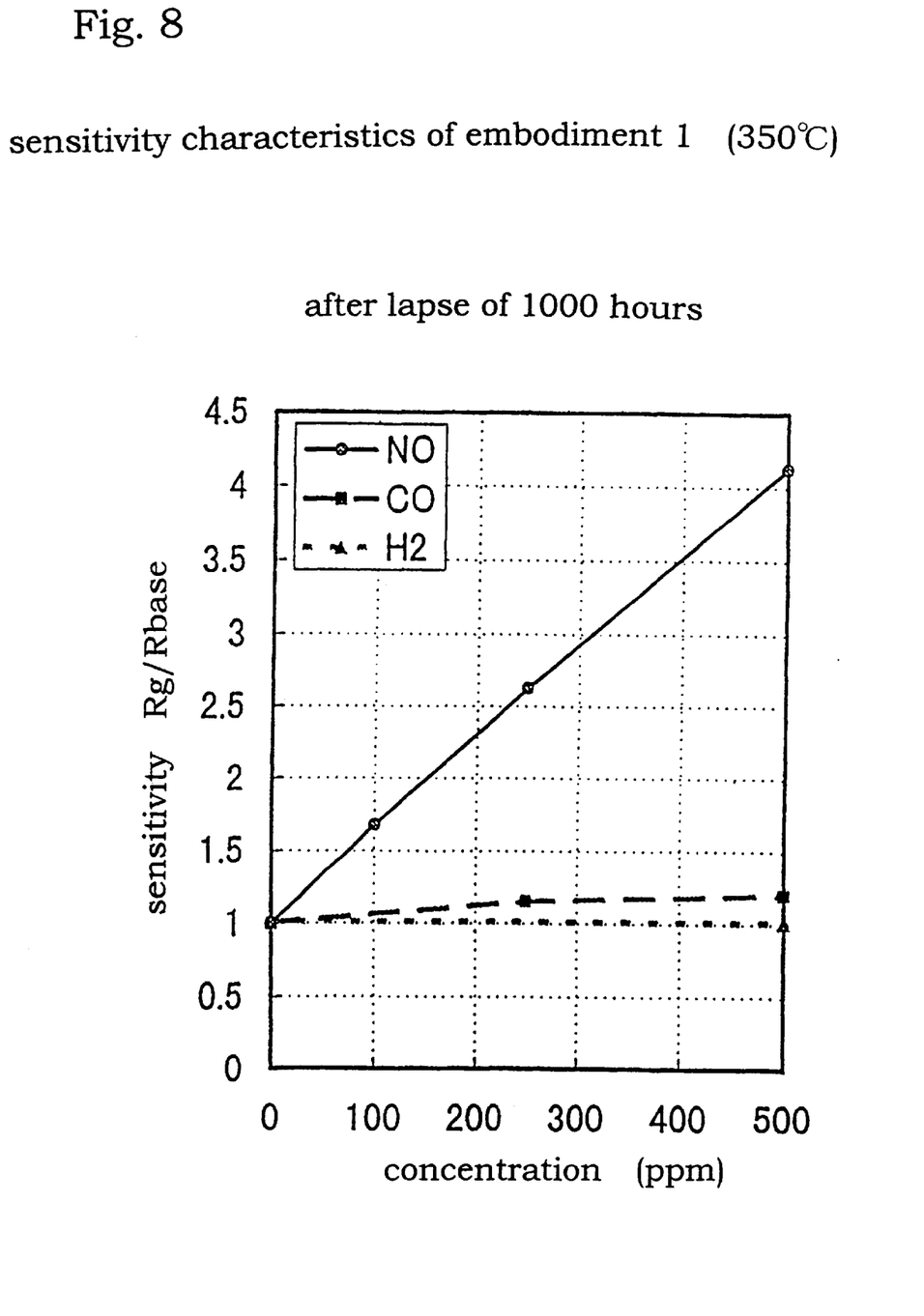
FIG. 8 is a graph showing results of measurements of sensitivities of the sensor according to the embodiment 1 on various gases at various concentrations (after lapse of 1000 hours)

The changes in the sensitivity of this sensor for various kinds of gas were checked before and after lapse of predetermined time periods. The base gas and the test gases were the same as those described hereinbefore concerning the operating temperature. The sensitivity immediately after the manufacture of the sensor element is shown in FIG. 7. The sensitivity thereof after the sensor element had been maintained at the operating temperature (350° C.) for 1000 hours is shown in FIG. 8. The results show that the selective sensing capability for CO against the so-called interfering gases $H_2$, CO does not change after use for the extended period of time. In this respect, the copper type complex oxide materials such as $Bi_2Sr_2CaCu_2O_{8+z}$ are inferior.

$Bi_2O_3$-NiO type

As demonstrated by the embodiment example 13 shown previously in Table 2, this type has a very high gas selectivity. Then, it may be understood that inclusion of Ni as an additive is desirable. Next, the results of studies concerning the amount of this additive (the ratio relative to Bi) will be described next.

The manufacturing conditions of this type of material corresponding to Table 1 are shown in Table 3, and the sensing properties corresponding to Table 2 in which the addition amount was varied are shown in Table 4.

TABLE 3 manufacturing conditions with different Ni addition amounts

| composition | preliminary sintering temp. | time period | main sintering temp. | time period |
|---|---|---|---|---|
| $(Bi_2O_3)_{0.99}(NiO)_{0.01}$ | 550° C. | 3 hrs. | 650° C. | 3 hrs. |
| $(Bi_2O_3)_{0.97}(NiO)_{0.03}$ | 550° C. | 3 hrs. | 650° C. | 3 hrs. |
| $(Bi_2O_3)_{0.95}(NiO)_{0.05}$ | 550° C. | 3 hrs. | 650° C. | 3 hrs. |
| $(Bi_2O_3)_{0.90}(NiO)_{0.10}$ | 550° C. | 3 hrs | 650° C. | 3 hrs. |
| $(Bi_2O_3)_{0.8}(NiO)_{0.2}$ | 550° C. | 3 hrs. | 700° C. | 3 hrs. |
| $(Bi_2O_3)_{0.5}(NiO)_{0.5}$ | 550° C. | 3 hrs. | 700° C. | 3 hrs. |
| $(Bi_2O_3)_{0.33}(NiO)_{0.66}$ | 550° C. | 3 hrs. | 750° C. | 3 hrs. |

TABLE 4 sensing properties with different Ni addition amounts

| composition | operating temp. | Rbase resistance value | NO 500 ppm | $H_2$ 500 ppm | CO 500 ppm |
|---|---|---|---|---|---|
| $(Bi_2O_3)_{0.99}(NiO)_{0.01}$ | 300° C. | 10 k | 3.04 | 1.00 | 1.06 |
| $(Bi_2O_3)_{0.97}(NiO)_{0.03}$ | 300° C. | 10 k | 6.28 | 1.03 | 1.12 |
| $(Bi_2O_3)_{0.95}(NiO)_{0.05}$ | 300° C. | 11 k | 6.29 | 1.03 | 1.16 |
| $(Bi_2O_3)_{0.90}(NiO)_{0.10}$ | 300° C. | 11 k | 6.04 | 1.00 | 1.06 |
| $(Bi_2O_3)_{0.8}(NiO)_{0.2}$ | 300° C. | 7.5 k | 4.20 | 1.00 | 1.00 |
| $(Bi_2O_3)_{0.5}(NiO)_{0.5}$ | 300° C. | 6.2 k | 2.80 | 1.00 | 1.05 |
| $(Bi_2O_3)_{0.33}(NiO)_{0.66}$ | 300° C. | 3.3 k | 2.10 | 1.05 | 1.10 |

As shown in Table 4, as for the ratio $NiO/Bi_2O_3$, it may be understood that the range of 0.03/0.97 to 0.2/0.8 is particularly desirable in the respect of the magnitude of NO sensitivity.

The material of Ni/Bi=1/1 (the ratio of Bi is 50 at. % in terms of the metallic elements conversion basis) too has NO selectivity. Yet, if Ni/Bi exceeds 1/1 thus resulting increased amount of NiO deposit, the sensitivities for CO and $H_2$ will develop, thus leading to deterioration of the sensitivity. This respect was confirmed separately.

Figure 9:
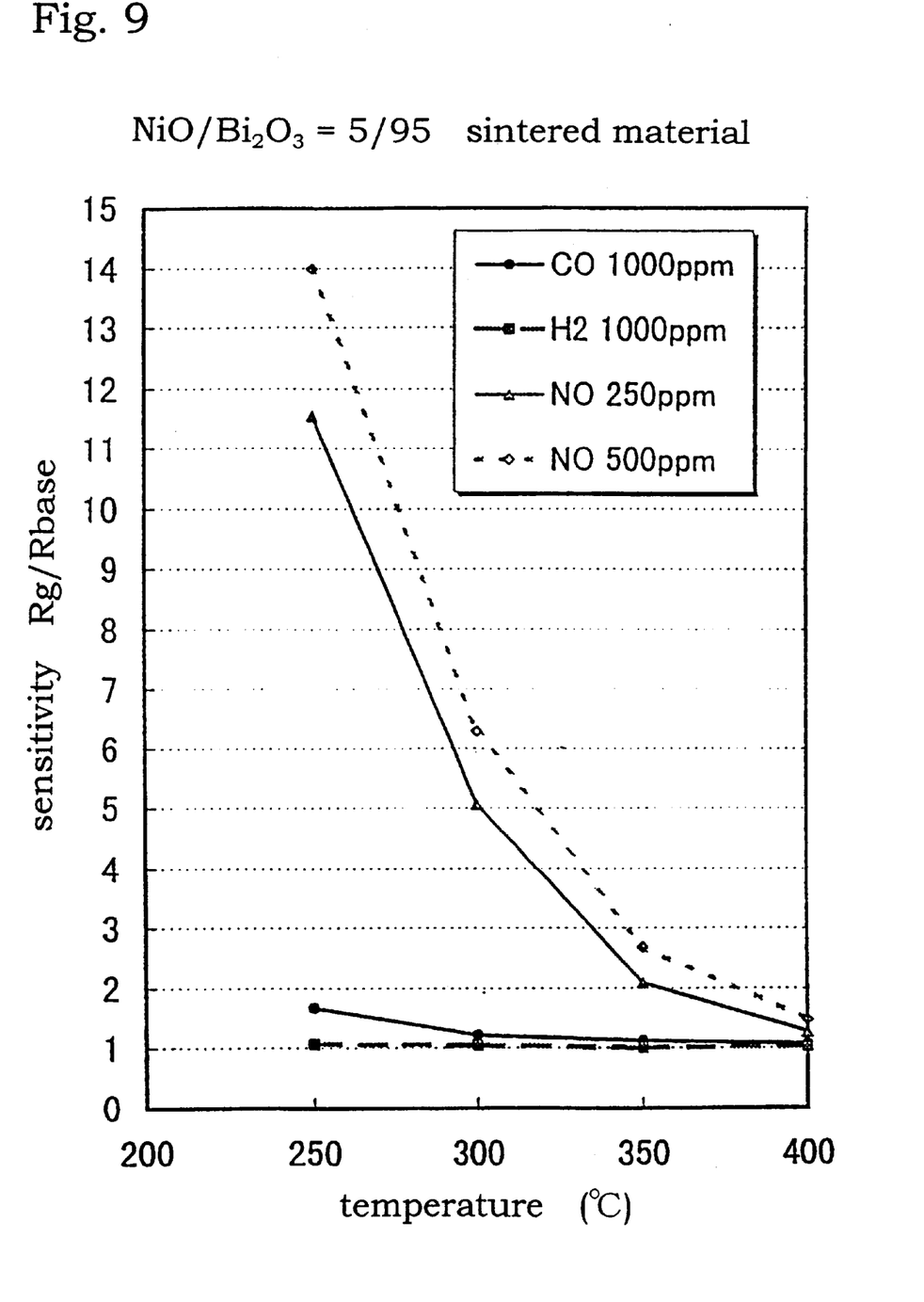
FIG. 9 is a graph showing results of measurements of a sensor of $NiO/Bi_2O_3=5/95$ on various kinds of gases at different measurement temperatures.

Now, concerning the material of $NiO/Bi_2O_3$=5/95 having the greatest selectivity, its sensor temperature property corresponding to FIG. 6 was determined and the results are shown in FIG. 9. In this case, however, the NO concentrations were 250 ppm and 500 ppm. The results show that the temperature range of 250 to 400° C. is desirable for the selective detection of NO. However, it was confirmed separately that this was usable at a temperature above the room temperature.

With this material, as the reduction of its NO sensitivity at a higher temperature is less than that of $Bi_2O_3$ without any additives, this makes its operation at higher temperature possible.

What is claimed is:

1. A method of detecting a nitrogen oxide comprising the steps of:

preparing a sensor element including a gas detecting portion and a pair of electrodes capable of detecting a change in conductivity of the gas detecting portion resulting from contact thereof with the nitrogen oxide, said gas detecting portion containing a metal oxide which contains 50 at. % or more of bismuth as determined by a conversion by the metallic elements basis and which has the $Bi_2O_3$ crystalline structure, the metal oxide having the p-type conductivity at a temperature range from a room temperature to 400° C.;

exposing said sensor element to a target gas suspected of nitrogen oxide contamination; and detecting the nitrogen oxide by detecting change in the conductivity of the gas detecting portion while maintaining the gas detection portion at said temperature range from a room temperature to 400° C.

2. A sensor element for detecting a nitrogen oxide comprising:

a gas detecting portion containing a metal oxide containing 50 at. % or more of bismuth as determined by a conversion by the metallic elements basis and having $Bi_2O_3$ crystalline structure, the metal oxide having the p-type conductivity at a temperature range from a room temperature to 400° C., wherein the gas detecting portion also contains, as an additive other than bismuth, one or more elements selected from the group consisting of metallic elements capable of having a valency not grater than 3;

electrodes capable of detecting a change in conductivity of the gas detecting portion resulting from contact thereof with the nitrogen oxide, the electrodes being electrically connected with said gas detecting portion; and heating means capable of maintaining the gas detecting portion at said temperature ranging from a room temperature to 400° C.

3. The method according to claim 1, wherein the gas detecting portion further contains, as an additive other than bismuth, one or more elements selected from the group consisting of metallic elements capable of having a valency not greater than 3.

4. The method according to claim 3, wherein said metallic elements capable of having a valency not greater than 3 comprise one or more elements selected from the group consisting of Ca, Sr, Ba, Cr, Mn, Fe, Co, Ni, Cu, Zn, and Cd.

5. The sensor element according to claim 4, wherein the said metallic elements comprise one or more elements selected from the group consisting of Ca, Sr, Ba, Cr, Mn, Fe, Co, Ni, Cu, Zn, and Cd.

6. The sensor element according to claim 2, wherein the gas detecting portion is formed by sintering of powder materials containing binder materials which do not affect the detection sensitivity.

7. The sensor element according to claim 2, wherein catalyst is provided for restricting any interfering gas other than the nitrogen oxide from reaching the gas detecting portion.

8. The sensor element according to claim 2, wherein a distance between the paired electrodes is set so that a resistance value of the gas detecting portion be $10^6$ Ω or less at said temperature range in the atmosphere.

9. The sensor element according to claim 2, wherein concerning the resistance value of the gas detecting portion interposed between the paired electrodes, the gas detecting portion further includes an electroconductive second phase which does not sense the nitrogen oxide so as to render a resistance value of the gas detecting portion $10^6$ Ω or less at said temperature range in the atmosphere.

10. The method according to claim 3, wherein said one or more elements selected from the group consisting of metallic elements capable of having a valency not greater than 3 is contained in the material forming the gas detecting portion at 10 at. % or less relative to the bismuth.

11. The method according to claim 1, wherein the gas detecting portion further contains, as an additive other than bismuth, one or more elements selected from the group consisting of In and Sn.

12. The method according to claim 11, wherein said one or more elements selected from the group consisting of In and Sn is contained in the material forming the gas detecting portion at 10 at. % or less relative to the bismuth.

13. The method according to claim 1, wherein the gas detecting portion further contains, as an additive other than bismuth, one or more elements selected from the group consisting of metallic elements capable of having a valency not greater than 3 and further contains one or more elements selected from the group consisting of In and Sn.

14. The method according to claim 13, wherein said one or more elements selected from the group consisting of metallic elements capable of having a valency not greater than 3 and said one or more elements selected from the group consisting of In and Sn are contained in the material forming the gas detecting portion at 10 at. % or less relative to the bismuth.

15. The sensor element according to claim 4, wherein said one or more elements selected from the group consisting of metallic elements capable of having a valency not greater than 3 is contained at 10 at. % or less relative to the bismuth.

16. The sensor element according to claim 2, wherein the gas detecting portion further contains, as an additive other than bismuth, one or more elements selected from the group consisting of In and Sn.

17. The sensor element according to claim 16, wherein said one or more elements selected from the group consisting of In and Sn is contained at 10 at. % or less relative to the bismuth.

18. The sensor element according to claim 2, wherein the gas detecting portion further contains, as an additive other than bismuth, one or more elements selected from the group consisting of metallic elements capable of having a valency not greater than 3 and further contains one or more elements selected from the group consisting of In and Sn.

19. The sensor element according to claim 18, wherein said one or more elements selected from the group consisting of metallic elements capable of having a valency not greater than 3 and said one or more elements selected from the group consisting of In and Sn are contained at 10 at. % or less relative to the bismuth.

* * * * *

UNITED STATES PATENT AND TRADEMARK OFFICE
CERTIFICATE OF CORRECTION

PATENT NO. : 6,306,351 B1
DATED : October 23, 2001
INVENTOR(S) : Shuzo Kudo et al.

It is certified that error appears in the above-identified patent and that said Letters Patent is hereby corrected as shown below:

Column 1,
Line 19, "needle to say" should read -- needless to say --.
Line 67, "above,." should read -- above. --.

Column 2,
Line 30, after "Bi" insert period -- (.) --.
Line 43, after "as well" insert period -- (.) --.

Column 3,
Line 3, "$B_2O_3$" should read -- $Bi_2O_3$ --.

Column 12,
Line 38, "grater than" should read -- greater than --.
Line 56, "according to claim 4" should read -- according to claim 2 --.

Column 14,
Line 6, "according to claim 4" should read -- according to claim 2 --.

Signed and Sealed this

Second Day of July, 2002

Attest:

JAMES E. ROGAN
Attesting Officer          Director of the United States Patent and Trademark Office